United States Patent [19]
Steiger et al.

[11] 4,000,124
[45] Dec. 28, 1976

[54] NOVEL LIQUID-CRYSTAL COMPOUNDS

[75] Inventors: Edward L. Steiger; Heinz J. Dietrich, both of Toledo, Ohio

[73] Assignee: Owens-Illinois, Inc., Toledo, Ohio

[22] Filed: May 18, 1971

[21] Appl. No.: 144,672

[52] U.S. Cl. .............. 260/206; 252/408; 350/150; 350/160 LC
[51] Int. Cl.$^2$ .............. C07C 105/00; G02F 1/28; G02N 31/00
[58] Field of Search .................... 260/206

[56] References Cited
UNITED STATES PATENTS

| | | | |
|---|---|---|---|
| 1,801,901 | 4/1931 | Britton et al. | 260/206 |
| 2,216,258 | 10/1940 | Weinand et al. | 260/192 |
| 2,782,185 | 2/1957 | Merian | 260/186 |
| 2,929,810 | 3/1960 | Horning | 260/206 |
| 3,170,910 | 2/1965 | Neracher et al. | 260/152 |

OTHER PUBLICATIONS

Woolfolk et al., Chemical Abstracts, vol. 57, 11841 (1962).
Kelker et al., Angew. Chem. Internat. Ed., vol. 9, pp. 962–963 (1970).

*Primary Examiner*—Floyd D. Higel
*Attorney, Agent, or Firm*—Donald Keith Wedding

[57] ABSTRACT

There is disclosed the preparation of novel liquid-crystal compounds of the structure:

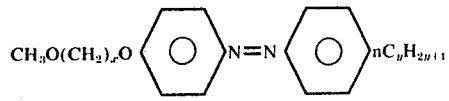

where $x$ and $y$ are the same or different integers of 1 to 10, typically 1 to 5.

2 Claims, No Drawings

NOVEL LIQUID-CRYSTAL COMPOUNDS

This invention relates to the preparation of novel mesomorphic compounds. More particularly, this invention relates to the preparation of mesomorphic compounds which may be utilized in display type devices.

Mesomorphic materials, typically referred to as liquid-crystal materials, are organic compounds in a transition state between crystalline solid and normal isotropic liquid forms. Such materials are well known in the prior art. Likewise, it is known in the prior art to use such liquid-crystal materials in display type devices.

In accordance with this invention, there is prepared novel liquid-crystal compounds of the structure:

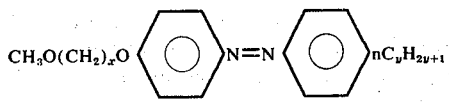

where $x$ and $y$ are the same or different integers of 1 to 10, typically 1 to 5.

The novel liquid-crystal compounds of this invention are prepared as follows:

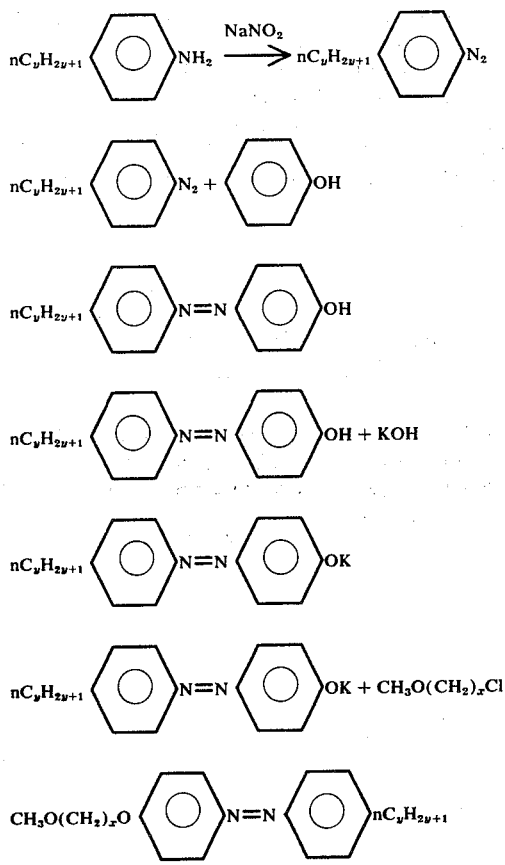

The para-n-alkyl aniline is commercially available. The methoxy alkyl halide is prepared by chlorination of a methoxy alcohol, $CH_3O(CH_2)_xOH$, where $x$ is an integer of 1 to 10, typically 1 to 5.

The liquid-crystal compounds prepared in accordance with this invention may be utilized in display devices, especially of the electronic type.

Such devices typically comprise a thin layer of liquid crystals sandwiched between two sheets of glass. Normally, the thin layer of liquid-crystal material is clear, but when an electric field is applied to it, some portions or regions of the material become turbulent so as to scatter light. By controlling the size and shape of the turbulent regions, images can be formed. Primarily, this effect is obtained by use of liquid-crystal materials of the nematic type.

In one particular embodiment, a liquid-crystal material is sandwiched as a dielectric in a parallel plate capacitor with one electrode transparent and the other electrode either transparent or reflecting. The liquid is kept between the electrodes by capillary action, since electrode spacings are of the order of ½ mil. An applied d.c. or low-frequency (less than 100 Hz.) field of more than 30,000 volts per centimeter changes the cell from transparent to turbulent in a few milliseconds. Depending upon the liquid-crystal composition, the opaque effect may remain even after the field is removed. In other words, an optical signal may be maintained with no applied power. The cell can be turned clear again by applying a higher-frequency (greater than 700 Hz.) signal. The sample remains clear after the signal is removed.

Additional embodiments of liquid-crystal electro-optical devices are disclosed and illustrated in U.S. Pat. Nos. 3,401,262 and 3,410,999; Proceedings of the IEEE, Vol. 56, No. 12, Dec., 1968, pages 2146 to 2149; The Glass Industry, Aug., 1968, pages 423 to 425; Chemical and Engineering News, Sept. 30, 1968, pages 32 and 33; Physics Today, July, 1970, pages 30 to 36; Electronics, July 6, 1970, pages 64 to 70; U.S. Pat. No. 3,322,485 to Williams.

It is also contemplated using the liquid-crystal compounds in a charge storage display/memory device, especially multiple gas discharge display/memory panels which have an electrical memory and which are capable of producing a visual display or representation of data such as numerals, letters, television display, radar displays, binary words, etc.

Multiple gas discharge display and/or memory panels of the type with which the present invention is especially concerned are characterized by an ionizable gaseous medium, usually a mixture of at least two gases at an appropriate gas pressure, in a thin gas chamber or space between a pair of opposed dielectric charge storage members which are backed by conductor (electrode) members, the conductor members backing each dielectric member being transversely oriented to define a plurality of discrete discharge volumes and constituting a discharge unit. In some prior art panels the discharge units are additionally defined by surrounding or confining physical structure such as by cells or apertures in perforated glass plates and the like so as to be physically isolated relative to other units. In either case, with or without the confining physical structure, charges (electrons, ions) produced upon ionization of the gas of a selected discharge unit, when proper alternating operating potentials are applied to selected conductors thereof, are collected upon the surfaces of the dielectric at specifically defined locations and constitute an electrical field opposing the electrical field which created them so as to terminate the discharge for the remainder of the half cycle and aid in the initiation of a discharge on a succeeding opposite half cycle of applied voltage, such charges as are stored constituting an electrical memory.

Thus, the dielectric layers prevent the passage of any conductive current from the conductor members to the gaseous medium and also serve as collecting surfaces for ionized gaseous medium charges (electrons, ions) during the alternate half cycles of the A.C. operating potentials, such charges collecting first on one elemental or discrete dielectric surface area and then on an opposing elemental or discrete dielectric surface area on alternate half cycles to constitute an electrical memory.

An example of a panel structure containing non-physically isolated or open discharge units is disclosed in U.S. Pat. No. 3,499,167 issued to Theodore C. Baker et al.

An Example of a panel containing physically isolated units is disclosed in the article by D. L. Bitzer and H. G. Slottow entitled "The Plasma Display Panel—A Digitally Addressable Display with Inherent Memory", Proceeding of the Fall Joint Computer Conference, IEEE, San Francisco, California, Nov. 1966, pages 541–547. Also reference is made to U.S. Pat. No. 3,559,190.

In the operation of the panel, a continuous volume of ionizable gas is confined between a pair of photoemissive dielectric surfaces backed by conductor arrays forming matrix elements. The cross conductor arrays may be orthogonally related (but any other configuration of conductor arrays may be used) to define a plurality of opposed pairs of charge storage areas on the surfaces of the dielectric bounding or confining the gas. Thus, for a conductor matrix having H rows and C columns the number of elemental discharge volumes will be the product H × C and the number of elemental or discrete areas will be twice the number of elemental discharge volumes.

The gas is one which produces light (if visual display is an objective) and a copious supply of charges (ions and electrons) during discharge. In an open cell Baker et al type panel, the gas pressure and the electric field are sufficient to laterally confine charges generated on discharge within elemental or discrete volumes of gas between opposed pairs of elemental or discrete dielectric areas within the perimeter of such areas, especially in a panel containing non-isolated units.

As described in the Baker et al. patent, the space between the dielectric surfaces occupied by the gas is such as to permit photons generated on discharge in a selected discrete or elemental volume of gas to pass freely through the gas space and strike surface areas of dielectric remote from the selected discrete volumes, such remote, photon struck dielectric surface areas thereby emitting electrons so as to condition other and more remote elemental volumes for discharges at a uniform applied potential.

With respect to the memory function of a given discharge panel, the allowable distance or spacing between the dielectric surfaces depends, inter alia, on the frequency of the alternating current supply, the distance typically being greater for lower frequencies.

In the practice of this invention, it is contemplated that a particular liquid crystal may be prepared and/or utilized alone or in combination with other liquid-crystal compositions of the same or different family, e.g. such as a mixture of 2 or more compositions. This may be especially desirable since mixtures of compounds may have lower transition temperatures than the individual compounds.

The diazotization step of this invention has been illustrated hereinbefore with reference to sodium nitrite. However, any source of nitrite anion ($NO_2^-$) may be used. Examples include not by way of limitation alkali nitrite such as sodium nitrite, potassium nitrite, and lithium nitrite; alkaline earth nitrite such as barium nitrite, calcium nitrite, and magnesium nitrite; inorganic nitrites such as ammonium nitrite; and organic nitrites such as alkyl nitrites of 1 to 10 carbons.

Likewise, although the phenolate salt formation has been illustrated hereinbefore with reference to potassium hydroxide, other strong inorganic bases may be utilized, especially alkali hydroxides such as sodium and lithium. Also alklai alkoxides are contemplated.

We claim:

1. A compound having the chemical structure

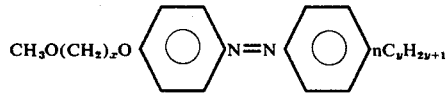

where $x$ and $y$ are the same or different integers of 1 to 10, said compound exhibiting liquid-crystal properties.

2. The invention of claim 1 wherein $x$ is an integer of 1 to 5 and $y$ is 4.

* * * * *